United States Patent [19]

Forgione et al.

[11] 4,088,125
[45] May 9, 1978

[54] METHOD AND APPARATUS FOR MONITORING SKIN POTENTIAL RESPONSE

[75] Inventors: Albert G. Forgione, Marblehead; Richard M. Horton, Duxbury, both of Mass.

[73] Assignee: Cyborg Corporation, Boston, Mass.

[21] Appl. No.: 743,096

[22] Filed: Nov. 19, 1976

[51] Int. Cl.$^2$ .............................................. A61B 5/05
[52] U.S. Cl. .................................. 128/2.1 Z; 35/22 R
[58] Field of Search ............. 128/2.1 Z, 2.1 B, 2.1 M, 128/2.1 R; 35/22 R

[56] References Cited

U.S. PATENT DOCUMENTS

| | | | |
|---|---|---|---|
| 2,829,638 | 4/1958 | Douglas | 128/2.1 Z |
| 2,902,030 | 9/1959 | Kennedy et al. | 128/2.1 M |
| 3,727,604 | 4/1973 | Sidwell et al. | 128/2.1 Z |
| 3,772,593 | 11/1973 | Sidhu | 128/2.1 Z |
| 3,901,214 | 8/1975 | Taaffe | 128/2.1 Z |
| 3,920,003 | 11/1975 | Ash et al. | 128/2.1 Z |
| 3,958,563 | 5/1976 | Fernandez et al. | 128/2.1 B |

Primary Examiner—Robert W. Michell
Assistant Examiner—Lee S. Cohen
Attorney, Agent, or Firm—Morse, Altman, Oates & Bello

[57] ABSTRACT

Biofeedback training of a subject may be achieved by monitoring the skin potential response of the subject and by shaping the monitored response so that a feedback signal is generated only if the response exceeds pre-established upper and lower limits which may be selectively increased or decreased. Biofeedback apparatus for implementing this technique includes electrodes for sensing the skin potential, an amplifier for amplifying the signal and feeding the signal into a pair of variable comparators which provide output when the response exceeds preset upper and lower limits. The outputs, in turn, provide a feedback signal either audio or visual, or to serve as inputs to auxiliary instrumentation. No feedback signal is produced as long as the monitored signal is within the selected limits. The magnitude of the responses may be quantified to the extent that they exceed the preset levels. The audio feedback signals may be recorded on a common audio cassette recorder. The method and the apparatus are useful in a clinical verbal interview.

9 Claims, 7 Drawing Figures

METHOD AND APPARATUS FOR MONITORING SKIN POTENTIAL RESPONSE

BACKGROUND OF THE INVENTION

1. Field of the Invention

This invention relates generally to biofeedback techniques and apparatus, and more particularly is directed towards a new and improved method and associated apparatus for monitoring skin potential response.

2. Description of the Prior Art

Conventional biofeedback techniques which are employed to monitor the degree of autonomic arousal do so by measuring changes in skin resistance of the subject. While the monitoring of changes in skin resistance provides useful information in various biofeedback procedures, it has a number of inherent drawbacks which limit its utility. For example, changes in skin resistance in response to stimulation generally are rather slow and a rlatively long period of time is involved between the initial stimulation and the return of the skin resistance to a normal condition after the stimulation has been removed. Furthermore, normal skin resistance tends to vary so that the base line resistance, or reference, will vary thereby introducing error into the system. Furthermore, the signal produced by measuring skin resistance changes in one direction only and thus carries relatively little information.

Accordingly, it is an object of the present invention to provide improvements in biofeedback techniques and instrumentation. Another object of this invention is to provide a quicker and more accurate means and technique for measuring the degree of autonomic arousal in response to stimulation. A still further object of this invention is to provide a method and associated apparatus for monitoring skin potential response and providing control means for shaping the skin potential response whereby signals are produced only when the detected signal exceeds certain preset limits, which limits may be increased or decreased selectively.

SUMMARY OF THE INVENTION

This invention features the method and associated apparatus for monitoring the skin potential of a subject in response to stimulation and providing shaping control over the skin potential response waves, whereby a feedback signal is generated only for the peaks of the waves. The control is variable so that by sequentially reducing the magnitude of the level at which the wave peaks generate a signal, a lower base line level of skin potential response can be gradually achieved. The apparatus includes sensors applied to the skin of the patient, amplifying means for amplifying the skin potential, filtering means, logarithmic amplifying means and variable comparators adapted to provide an output signal only when the peaks of the input signals exceed certain predetermined levels which are controlled manually. Output means connected to the comparators provide a feedback signal to the subject when the wave peaks of the signal exceed the preset limits.

DETAILED DESCRIPTION OF THE PREFERRED EMBODIMENT

Figure 2:
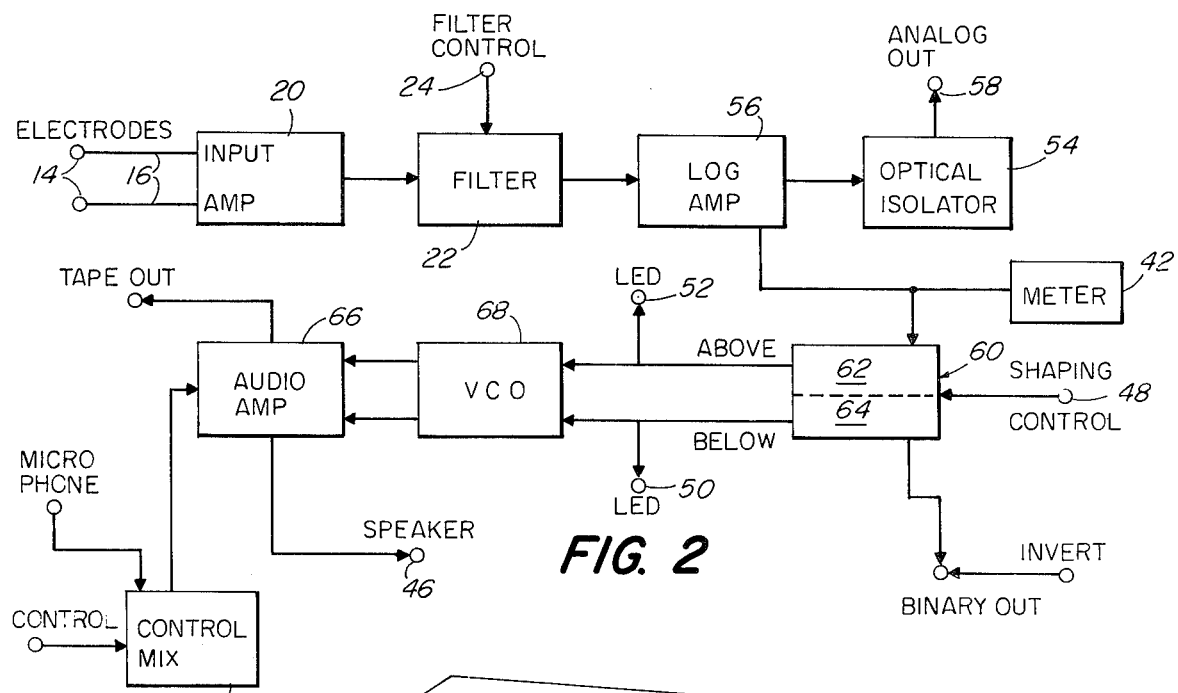
FIG. 2 is a block diagram of a skin potential response system made according to the invention, FIGS. 3(a), (b) and (c) are wave forms showing typical skin potential response signals.
Figure 1:
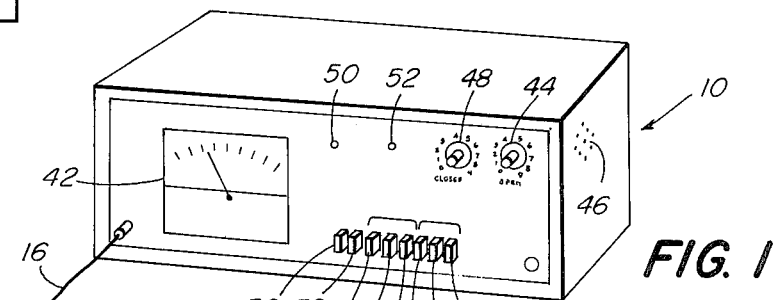
FIG. 1 is a view in perspective of a skin potential response apparatus made according to the invention.

Referring now to the drawings and to FIG. 1 in particular, the reference character 10 generally indicates a biofeedback apparatus for monitoring the skin potential response of a subject 12 by connecting electrodes 14 to the subject through a cord connection 16. Preferably the skin potential response is monitored between the palm of the hand and the back of the hand and/or the forearm of the dominant hand. The palm provides the active electrode site, while the back of the hand or the forearm provides the reference electrode site.

Figure 3A:
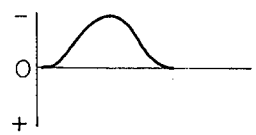
Figure 3B:
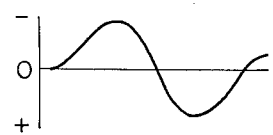
Figure 3C:
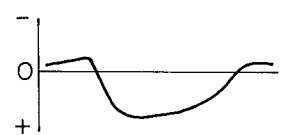
Figure 5:
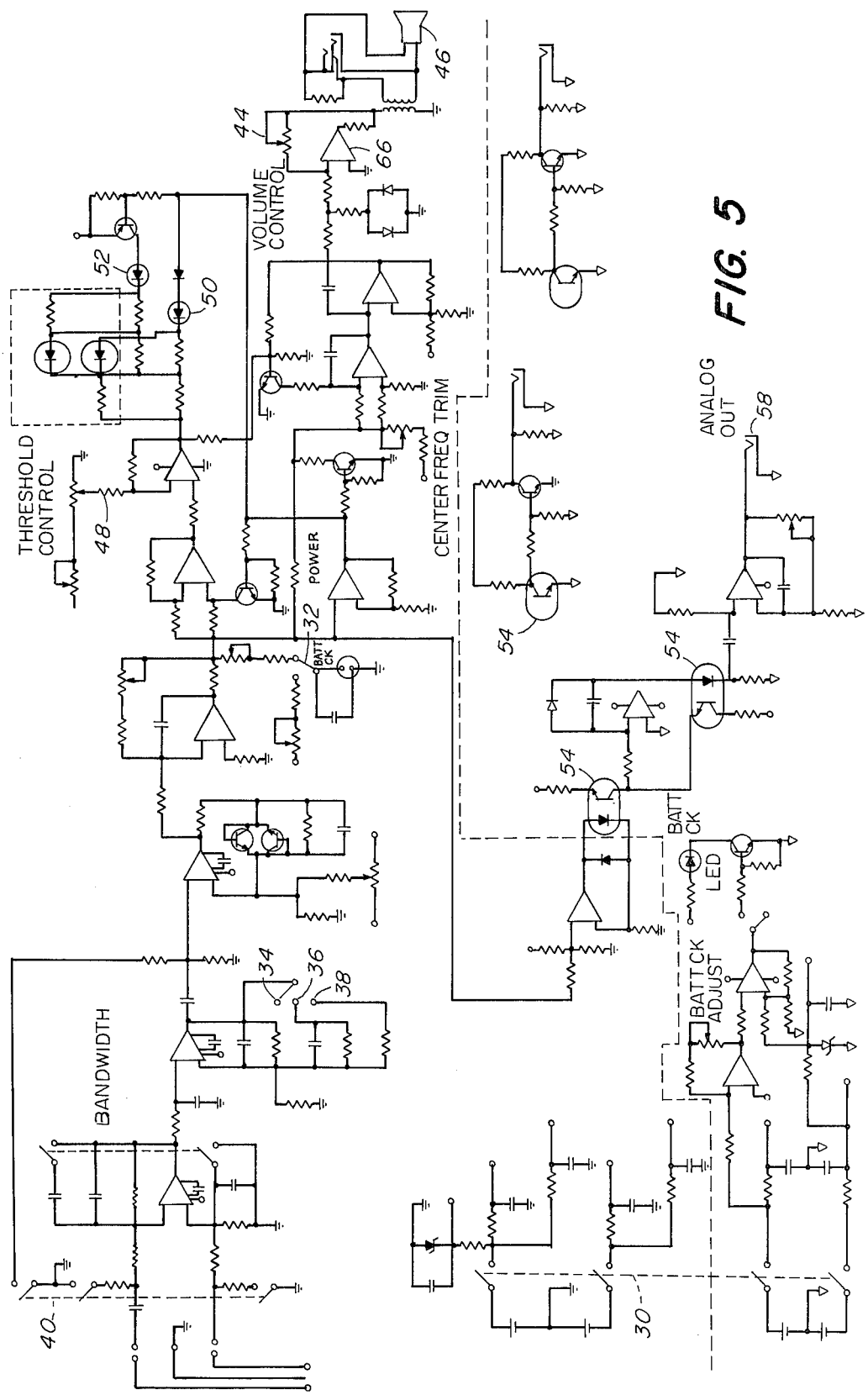

The skin potential response, in practice, is a minute voltage potential, and, depending upon the intensity of the applied stimulation, the response may occur in any of the three forms shown in FIGS. 3(a), (b) and (c). In FIG. 3(a) there is shown a negative wave form which is produced by mild stimulation; FIG. 3 (b) shows a biphasic wave resulting from an intermediate level of stimulation, while FIG. 3(c) shows a positive wave form resulting from an intense stimulation. The skin potential response has been found to reflect the degree of autonomic arousal in a subject and provides significant information with respect to the subject beyond that available to the monitoring of changes in skin resistance.

It has been found that the amplitude and the frequency of the wave form generated by skin potential response is related to sympathetic arousal. The positive wave of the skin potential response is believed to be an indicator of the defense reflex, while the negative wave is an indicator of the orienting relfex. The positive wave has been found to increase monotonically with the intensity of sound and electric shock applied to the subject, there being a direct relation between the stimulus and the amplitude of the wave. The positive wave persists under conditions in which aversive stimulation is anticipated. In addition, the high frequency of skin potential responses associated with stressful conditions disappear when the external stresses are removed.

The skin potential response signal is sinusoidal, as will be seen in FIG. 3, and has a base line of zero to which it always returns when recorded with AC (time constant). This characteristic is extremely useful insofar as with a zero base line the signal always returns to the same point, thereby eliminating a source of error which is common to a skin resistance monitoring system or when skin potential is monitored with DC (direct current). Insofar as the signal goes both up and down, two polarities are available to provide more information, and since no current is applied to the skin, instrumentation is simplified. Skin potential response provides a measurement and permits the training of direct autonomic responses rather than an indirect somatic muscular index relaxation, as is the case with an EMG feedback. Further, the skin potential response is measured in voltages much larger than with EMG, being on the order of one thousandth of a volt rather than a millionth of a volt, whereby the skin potential response signal is much less susceptible to electrical and motion interference as is the case with an EMG system.

The skin potential response signals detected by the electrodes 14 are fed first into an input amplifier 20 which amplifies the signal and delivers it to a filter 22.

Preferably the input amplifier 20 is an amplifier having an input range of ± 0.3 to ± 30 millivolts. The filter 22 serves to separate the monitored skin potential response signal from background noise and is provided with filter controls 24 in the form of switches and, typically, the system may have two filter settings 0.2Hz and 1Hz, operated by the push buttons 26 and 28 on the front of the cabinet. In addition to the filter setting switches 26 and 28, the front panel of the unit also includes a push button switch 30 which turns the system on and off, a push button switch 32 providing a battery checking function, three push buttons 34, 36 and 38 for changing the sensitivity of the system through ranges, for example, ± 30, ± 3 and ± 0.3 mV. A final push button switch 40 is connected to the filter circuit and functions as an initial filter setting.

The control panel also includes a pseudo-logarithmic meter 42 providing a visual display of the monitored signal, a volume control knob 44 controlling a loudspeaker 46, which preferably is built into the cabinet, and a shaping control knob 48, the function of which will be described more fully below. The control panel also includes a pair of indicator lights 50 and 52 which, preferably, are red and green light emitting diodes providing a visual feedback indication whenever the skin potential response goes above or below variable levels set into the system by the shaping conrol knob 48.

The output of the filter 22 is then fed to a pseudo-logarithmic amplifier 56 which allows greater amplification of the signal near the baseline, thereby providing a wider range over the control of the signal. The logarithmic amplifier provides an output to the meter 42 and detector 60 as well as through an optical isolator 54 to a terminal 58. The terminal 58 may be employed to operate various auxiliary equipment, such as recorders, or the like, while the detector 60 provides the shaping control over the skin potential response of the subject.

The detector 60 is in the form of a pair of comparators 62 and 64, one for the positive portion of the monitored signal and the other for the negative portion thereof. The shaping control knob 48 is connected to the detector by means of which the reference levels for the comparators 62 and 64 may be selectively increased or decreased at the same time. The comparators 62 and 64 are set by means of the control 48 to generate an output signal only when the amplitude of the monitored signal goes above or below levels set by the shaping control 48. As long as the monitored signal is within the limits set by the shaping control, the comparators do not produce an output and there will be no feedback signal to the subject. However, if the monitored signal goes above or below the level set by the shaping control, a feedback signal is generated so as to illuminate the light emitting diodes 50 and 52 for the visual indicators as well as to operate the audio output comprised of the speaker 46 driven by an audio amplifier 66 and a voltage controlled oscillator 68. The audio portion of the system generates a decreasing tone pitch when the negative wave of the signal falls below the level set by the shaping control and produces an increasing tone pitch when the positive wave exceeds the level set by the shaping control.

The feedback signal may also be fed through a mixer 72 for recording the audio feedback output, and in this fashion record the iteraction of the subject, the technician, and the responses produced. By recording the results of the system, it is possible to measure the magnitude of responses and an ordinary tape recorder may be used for this purpose.

Figure 4:
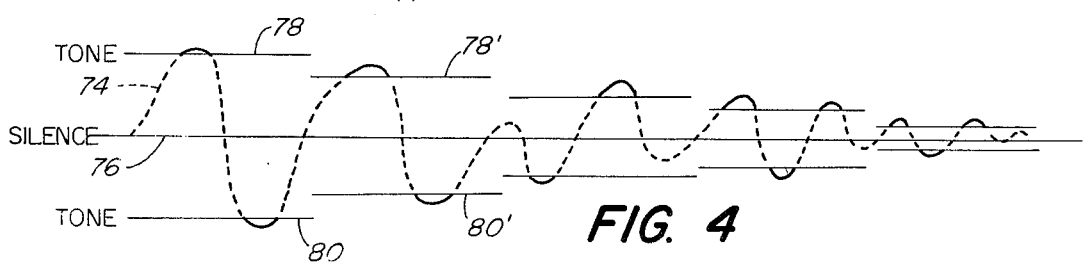
FIG. 4 is a schematic diagram showing a decreasing skin potential response wave and decreasing feedback peak levels, and, FIG. 5 is a circuit diagram of the system.

Operation of the system is, in part, illustrated by reference to FIG. 4. In FIG. 4 the monitored skin potential response signal is represented by a wave form 74 alternating above and below a zero base line 76. Upper and lower limit lines 78 and 80, respectively, represent different settings by the shaping control 48 which vary the reference signals to the comparators 62 and 64 in the detector 60. As long as the peaks of the wave form 74 remain within the limit lines 78 and 80 there is no feedback signal since the comparators are not actuated and the loudspeaker 46 remains silent and the lights 50 and 52 remain off. However, if the signal 74 goes above the limit line 78 or below the limit line 80, the comparators 62 and 64 will be actuated to generate a feedback signal both audio and visual. Initially, the wave form may be relatively large in amplitude and biphasic, indicating both negative and positive response to stimulation. The subject may learn to relax by lowering the magnitude of the wave 74 through manipulation of the shaping control which, as shown in FIG. 4, may be done by gradually reducing the levels at which the peaks of the wave form produce a feedback signal. Thus, in FIG. 4, the limit lines 78' and 80' indicate a reduced setting of the shaping control, thereby reducing the envelope within which the wave form may oscillate without producing a feedback signal. By sequentially reducing the envelope, the range may be reduced to audibly feed back skin potential response peaks of lesser magnitude. In this way reinforcement of successive approximations to the desired low arousal level is made possible. Learning criteria for each individual may be adjusted to both the degree of arousal and the speed of learning. The method and apparatus utilizing the skin potential response of the subject in a shaping control program may be used to measure anxiety responses to verbal stimuli and to monitor trained relaxation, as well as to provide exact measurements of the signal. Using a tape recorder in conjunction with such a program, a permanent record can be made of the verbal response and the simultaneous skin potential response and audio response. The technique measures and permits training of direct autonomic response rather than an indirect somatic muscular index of relaxation and will yield a more general systemic measurement rather than specific muscle areas thought to reflect an overall body-wide condition. The skin potential response technique measures voltage in much greater levels than other similar systems which thus makes the system much less susceptible to interference.

In addition to the foregoing, the system may be modified to generate a feedback signal to the subject whenever the skin potential signal fails to exceed the reference signals (i.e., stays within reference limits) by means of allowing the subject to reduce his muscle tension which may be recorded and fed back to the subject by means of an EMG system. Such a technique is useful in training total somatic relaxation by first establishing autonomic quiescence then allowing muscle relaxation training. (Making muscle relaxation training contingent upon autonomic quiescence, i.e., low magnitude skin potential response).

Having thus described the invention, what we claim and desire to obtain by Letters Patent of the United States is:

1. The method of training a subject in the control of autonomic functions of the subject comprising the steps of (a) monitoring the alternating skin potential signals having positive and negative components with respect to zero potential produced by the subject in response to stimulation of the subject, (b) comparing said alternating skin potential signals to a variable reference signal having positive and negative components with respect to zero, and, (c) generating a feedback signal to said subject whenever said positive and negative components of said skin potential signals are out of comparison with said positive and negative components of said reference signal respectively.

2. The method of claim 1 wherein said feedback signals are generated whenever the components of said skin potential signals exceed the components of said reference signal.

3. The method of claim 1 wherein said feedback signals are generated whenever the components of said skin potential signals are less than the components of said reference signal.

4. The method of claim 1 wherein said skin potential signals are compared to positive and negative reference signals, the amplitudes of which may be varied with respect to a zero baseline of said skin potential signal.

5. The method of claim 4, including the steps of successively reducing the amplitudes of said reference signals.

6. Apparatus for training a subject in the control of autonomic functions of the subject, comprising (a) electrode means connectable to said subject for detecting the alternating skin potential signals having positive and negative components with respect to zero potential generated by said subject in response to stimulation of said subject, (b) electronic signal processing means connected to said electrode means for processing said skin potential signals, (c) said processing means including variable reference means for comparing said skin potential signals to variable reference signals having positive and negative components with respect to zero and generating feedback signals only when said positive and negative components of said skin potential signals are out of comparison with said positive and negative components of said reference signals respectively.

7. Apparatus, accordng to claim 6, wherein said reference means includes a pair of variable comparators, said comparators including limit means adapted to pass the positive and negative components of said alternating signals that exceed pre-set limits.

8. Apparatus, according to claim 6, wherein said reference means includes circuit means adapted to generate feedback signals only when the components of said skin potential signals exceed the components of said reference signals.

9. Apparatus, according to claim 6, wherein said reference means includes circuit means adatepd to generate feedback signals only when the components of said skin potential signals are less than the components of said reference signals.

* * * * *